US006485977B1

(12) United States Patent
Collmer et al.

(10) Patent No.: US 6,485,977 B1
(45) Date of Patent: Nov. 26, 2002

(54) RECOMBINANT CONSTRUCTS AND TECHNIQUES FOR DELIVERING TO EUCARYOTIC CELLS BACTERIAL PROTEINS THAT ARE SECRETED VIA TYPE III SECRETION SYSTEMS

(75) Inventors: Alan Collmer, Ithaca, NY (US); Steven V. Beer, Ithaca, NY (US)

(73) Assignee: Cornell Research Foundation, Inc., Itchaca, NY (US)

( * ) Notice: Subject to any disclaimer, the term of this patent is extended or adjusted under 35 U.S.C. 154(b) by 72 days.

(21) Appl. No.: 09/660,742

(22) Filed: Sep. 13, 2000

Related U.S. Application Data

(60) Provisional application No. 60/153,507, filed on Sep. 13, 1999.

(51) Int. Cl.$^7$ ...................... C12N 15/867; C12N 15/63; C12N 15/64; C12N 5/10
(52) U.S. Cl. .................... 435/455; 435/320.1; 435/456; 435/69.1; 435/69.7; 435/325; 536/23.1; 536/23.4; 536/24.1
(58) Field of Search ............................. 435/320.1, 455, 435/456, 69.1, 69.7, 325; 536/23.1, 23.4, 24.1

(56) References Cited

U.S. PATENT DOCUMENTS 6,221,355 B1 * 4/2001 Dowdy .................... 424/192.1

OTHER PUBLICATIONS

Fawell et al., "Tat–Mediated Delivery of Heterologous Proteins Into Cells," *Proc. Natl. Acad. Sci. USA*, 91:664:668 (1994).
Alfano et al., "The Type III (Hrp) Secrection Pathway of Plant Pathogenic Bacteria: Trafficking Harpins, Avr Proteins, and Death," *J. Bacteriol.*, 179(18):5655–5662 (1997).
Rossier et al., "The Xanthomonas Hrp Type III System Secretes Proteins From Plant and Mammalian Bacterial Pathogens," *Proc. Natl. Acad. Sci. USA* 96:9368–9373 (1999).
Galán et al., "Type III Secretion Machines: Bacterial Devices for Protein Delivery into Host Cells," *Science* 284:1322–1328 (1999).
Phelan et al., "Intercellular Delivery of Functional p53 by the Herpesvirus Protein VP22," *Nature Biotechnology* 16:440–443 (1998).
Chen et al., "Selective Killing of Transformed Cells by Cyclin/Cyclin–Dependent Kinase 2 Antagonists," *Proc. Natl. Acad. Sci. USA* 96:4325–4329 (1999).
Alfano et al., "The *Pseudomonas syringae* Hrp Pathogenicity Island Has a Tripartite Mosaic Structure Composed of a Cluster of Type III Secretion Genes Bounded by Exchangeable Effector and Conserved Effector Loci That Contribute to Parasitic Fitness and Pathogenicity in Plants," *PNAS* 97:4856–4861 (2000).
Collmer et al., "*Pseudomonas syringae* Hrp Type III Secretion System and Effector Proteins, " *PNAS* 97:8770–8777 (2000).
Schwarze et al., "Protein Transduction: Unrestricted Delivery into all Cells?" *Trends In Cell Biology* 10:290–295 (2000).
Schwarze et al., "In Vivo Protein Transduction: Delivery of a Biologically Active Protein into the Mouse," *Science* 285:1569–1572 (1999).
Anderson et al., "Reciprocal Secretion of Proteins by the Bacterial Type III Machines of Plant and Animal Pathogens Suggests Universal Recognition of mRNA Targeting Signals," *PNAS* 96:12839–12843 (1999).

\* cited by examiner

*Primary Examiner*—David Guzo
(74) *Attorney, Agent, or Firm*—Nixon Peabody LLP

(57) ABSTRACT

The present invention relates to a method for delivering effector proteins into a target cell. This method involves introducing into the target cell an effector protein fused to a protein transduction domain of a human immunodeficiency virus TAT protein or derivatives or functional analogs thereof. The present invention also relates to a fusion protein including an effector protein fused to a protein transduction domain of a human immunodeficiency virus TAT protein or derivatives or functional analogs thereof. Another aspect of the present invention relates to a DNA construct including a first DNA molecule encoding an effector protein and a second DNA molecule operatively associated with the first DNA molecule and encoding a protein transduction domain of a human immunodeficiency virus TAT protein or derivatives or functional analogs thereof and its use in a method for delivering effector proteins into a target cell.

11 Claims, 4 Drawing Sheets

SEQUENCE LISTING

<160> NUMBER OF SEQ ID NOS: 14

<210> SEQ ID NO 1
<211> LENGTH: 11
<212> TYPE: PRT
<213> ORGANISM: Homo sapiens

<400> SEQUENCE: 1

Tyr Gly Arg Lys Lys Arg Arg Gln Arg Arg Arg
1               5                   10

<210> SEQ ID NO 2
<211> LENGTH: 68
<212> TYPE: DNA

<213> ORGANISM: Artificial Sequence
<220> FEATURE:
<223> OTHER INFORMATION: Description of Artificial Sequence:
      Oligonucleotide

<400> SEQUENCE: 2
ccatgggcca tcatcatcat catcatcatc atcatcacag cagcggccat atcgaaggtc    60
gtcatatg                                                             68

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence:
      Polypeptide

<400> SEQUENCE: 3

Met Gly His His His His His His His His His Ser Ser Gly His
 1               5                  10                  15

Ile Glu Gly Arg His Met
            20

<210> SEQ ID NO 4
<211> LENGTH: 71
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
ccatgggcca tcaccatcac catcacggct atggccgtaa aaacgccgt cagcgccgtc     60 gcggtcatat g                                                         71

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence:
      Polypeptide

<400> SEQUENCE: 5

Met Gly His His His His His His Gly Tyr Gly Arg Lys Lys Arg Arg
 1               5                  10                  15

Gln Arg Arg Arg Gly His Met
            20

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ggatcaccat gggccatcac catcaccatc acggctatgg ccgtagtcg                49

<210> SEQ ID NO 7
<211> LENGTH: 49
<212> TYPE: DNA
<213> ORGANISM: Artificial Sequence
<220> FEATURE:

```
<223> OTHER INFORMATION: Description of Artificial Sequence:
      Oligonucleotide

<400> SEQUENCE: 7
cgactacggc catagccgtg atggtgatgg tgatggccca tggtgatcc              49

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
cggctatggc cgtaaaaaac gccgtcagcg ccgtcgcggt catatgttac tagc         54

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gctagtaaca tatgaccgcg acggcgctga cggcgttttt tacggccata gccg         54

<210> SEQ ID NO 10
<211> LENGTH: 170
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
ggatcaccat gggccatcac catcaccatc acggctatgg ccgtaaaaaa cgccgtcagc   60
gccgtcgcgg tcatatgtta ctagccctag tggtacccgg tagtggtagt ggtagtgccg  120
ataccggcat tttttgcggc agtcgcggca gcgccagtat acaatgatcg              170

<210> SEQ ID NO 11
<211> LENGTH: 1128
<212> TYPE: DNA
<213> ORGANISM: Pseudomonas syringae

<400> SEQUENCE: 11 gtgaaccctca tccatgcacg cttctccagc gtagaagcgc tcagacattc aaacgttgat   60
attcaggcaa tcaaatccga gggtcagttg gaagtcaacg gcaagcgtta cgagattcgt  120
gcggccgctg acggctcaat cgcggtcctc agacccgatc aacagtccaa agcagacaag  180
ttcttcaaag gcgcagcgca tcttattggc ggacaaagcc agcgtgccca aatagcccag  240
gtactcaacg agaaagcggc ggcagttcca cgcctggaca gaatgttggg cagacgcttc  300
gatctggaga agggcggaag tagcgctgtg ggcgccgcaa tcaaggctgc cgacagccga  360
ctgacatcaa aacagacatt tgccagcttc agcaatggg ctgaaaaagc tgaggcgctc  420
gggcgatacc gaaatcggta tctacatgat ctacaagagg acacgccag acacaacgcc  480 tatgaatgcg gcagagtcaa gaacattacc tggaaacgct acaggctctc gataacaaga  540
aaaaccttat catacgcccc gcagatccat gatgatcggg aagaggaaga gcttgatctg  600
ggccgataca tcgctgaaga cagaaatgcc agaaccggct ttttttagaat ggttcctaaa  660
```

```
gaccaacgcg cacctgagac aaactcggga cgacttacca ttggtgtaga acctaaatat    720
ggagcgcagt tggccctcgc aatggcaacc ctgatggaca agcacaaatc tgtgacacaa    780
ggtaaagtcg tcggtccggc aaaatatggc cagcaaactg actctgccat tctttacata    840
aatggtgatc ttgcaaaagc agtaaaactg gcgaaaagc tgaaaaagct gagcggtatc     900
cctcctgaag gattcgtcga acatacaccg ctaagcatgc agtcgacggg tctcggtctt    960
tcttatgccg agtcggttga agggcagcct tccagccacg gacaggcgag aacacacgtt   1020
atcatggatg ccttgaaagg ccagggcccc atggagaaca gactcaaaat ggcgctggca   1080
gaaagaggct atgacccgga aaatccggcg ctcagggcgc gaaactga                1128
```

<210> SEQ ID NO 12
<211> LENGTH: 375
<212> TYPE: PRT
<213> ORGANISM: Pseudomonas syringae

<400> SEQUENCE: 12

```
Val Asn Pro Ile His Ala Arg Phe Ser Ser Val Glu Ala Leu Arg His
  1               5                  10                  15

Ser Asn Val Asp Ile Gln Ala Ile Lys Ser Glu Gly Gln Leu Glu Val
             20                  25                  30

Asn Gly Lys Arg Tyr Glu Ile Arg Ala Ala Ala Asp Gly Ser Ile Ala
         35                  40                  45

Val Leu Arg Pro Asp Gln Gln Ser Lys Ala Asp Lys Phe Phe Lys Gly
     50                  55                  60

Ala Ala His Leu Ile Gly Gly Gln Ser Gln Arg Ala Gln Ile Ala Gln
 65                  70                  75                  80

Val Leu Asn Glu Lys Ala Ala Ala Val Pro Arg Leu Asp Arg Met Leu
                 85                  90                  95

Gly Arg Arg Phe Asp Leu Glu Lys Gly Gly Ser Ser Ala Val Gly Ala
            100                 105                 110

Ala Ile Lys Ala Ala Asp Ser Arg Leu Thr Ser Lys Gln Thr Phe Ala
        115                 120                 125

Ser Phe Gln Gln Trp Ala Glu Lys Ala Glu Ala Leu Gly Arg Tyr Arg
    130                 135                 140

Asn Arg Tyr Leu His Asp Leu Gln Glu Gly His Ala Arg His Asn Ala
145                 150                 155                 160

Tyr Glu Cys Gly Arg Val Lys Asn Ile Thr Trp Lys Arg Tyr Arg Leu
                165                 170                 175

Ser Ile Thr Arg Lys Thr Leu Ser Tyr Ala Pro Gln Ile His Asp Asp
            180                 185                 190

Arg Glu Glu Glu Leu Asp Leu Gly Arg Tyr Ile Ala Glu Asp Arg
        195                 200                 205

Asn Ala Arg Thr Gly Phe Phe Arg Met Val Pro Lys Asp Gln Arg Ala
    210                 215                 220

Pro Glu Thr Asn Ser Gly Arg Leu Thr Ile Gly Val Glu Pro Lys Tyr
225                 230                 235                 240

Gly Ala Gln Leu Ala Leu Ala Met Ala Thr Leu Met Asp Lys His Lys
                245                 250                 255

Ser Val Thr Gln Gly Lys Val Val Gly Pro Ala Lys Tyr Gly Gln Gln
            260                 265                 270

Thr Asp Ser Ala Ile Leu Tyr Ile Asn Gly Asp Leu Ala Lys Ala Val
        275                 280                 285
```

```
Lys Leu Gly Glu Lys Leu Lys Lys Leu Ser Gly Ile Pro Pro Glu Gly
    290                 295                 300

Phe Val Glu His Thr Pro Leu Ser Met Gln Ser Thr Gly Leu Gly Leu
305                 310                 315                 320

Ser Tyr Ala Glu Ser Val Glu Gly Gln Pro Ser Ser His Gly Gln Ala
                325                 330                 335

Arg Thr His Val Ile Met Asp Ala Leu Lys Gly Gln Gly Pro Met Glu
            340                 345                 350

Asn Arg Leu Lys Met Ala Leu Ala Glu Arg Gly Tyr Asp Pro Glu Asn
        355                 360                 365

Pro Ala Leu Arg Ala Arg Asn
    370                 375

<210> SEQ ID NO 13
<211> LENGTH: 1461
<212> TYPE: DNA
<213> ORGANISM: Pseudomonas syringae

<400> SEQUENCE: 13
atgcacatca accgacgcgt ccaacaaccg cctgtgactg cgacggatag ctttcggaca     60
gcgtccgacg cgtctcttgc ctccagctct gtgcgatctg tcagctccga tcagcaacgc    120
gagataaatg cgattgccga ttacctgaca gatcatgtgt tcgctgcgca taaactgccg    180
ccggccgatt cggctgatgg ccaagctgca gttgacgtac acaatgcgca gatcactgcg    240
ctgatcgaga cgcgcgccag ccgcctgcac ttcgaagggg aaaccccggc aaccatcgcc    300
gacaccttcg ccaaggcgga aaagctcgac cgattggcga cgactacatc aggcgcgttg    360
cgggcgacgc cctttgccat ggcctcgttg cttcagtaca tgcagcctgc gatcaacaag    420
ggcgattggc tgccggctcc gctcaaaccg ctgacccgc tcatttccgg agcgctgtcg    480
ggcgccatgg accaggtggg caccaagatg atggaccgcg cgacgggtga tctgcattac    540
ctgagcgcct cgccggacag gctccacgat gcgatggccg cttcggtgaa cgccactcg    600 ccaagccttg ctcgacaggt tctggacacg ggggttgcgg ttcagacgta ctcggcgcgc    660
aacgccgtac gtaccgtatt ggctccggca ctggcgtcca gacccgccgt gcagggtgct    720
gtggaccttg tgtatcgat ggcgggtggt ctggctgcca acgcaggctt tggcaaccgc    780
ctgctcagtg tgcagtcgcg tgatcaccag cgtggcggtg cattagtgct cggtttgaag    840
gataaagagc ccaaggctca actgagcgaa gaaaacgact ggctcgaggc ttataaagca    900
atcaaatcgg ccagctactc gggtgcggcg ctcaacgctg gcaagcggat ggccggtctg    960
ccactggata tggcgaccga cgcaatgggt gcggtaagaa gcctggtgtc agcgtccagc   1020
ctgacccaaa acgtctggc cctggcgggt ggctttgcag gggtaggcaa gttgcaggag   1080
atggcgacga aaaatatcac cgacccggcg accaaggccg cggtcagtca gttgaccaac   1140
ctggcaggtt cggcagccgt tttcgcaggc tggaccacgg ccgcgctgac aaccgatccc   1200
gcggtgaaaa aagccgagtc gttcatacag gacacggtga atcgactgc atccagtacc   1260 acaggctacg tagccgacca gaccgtcaaa ctggcgaaga ccgtcaaaga catgggcggg   1320
gaggcgatca cccataccgg cgccagcttg cgcaatacgg tcaataacct gcgtcaacgc   1380
ccggctcgtg aagctgatat agaagagggg ggcacggcgg cttctccaag tgaaataccg   1440
tttcggccta tgcggtcgta a                                             1461

<210> SEQ ID NO 14
<211> LENGTH: 486
```

-continued

```
<212> TYPE: PRT
<213> ORGANISM: Pseudomonas syringae

<400> SEQUENCE: 14

Met His Ile Asn Arg Arg Val Gln Gln Pro Val Thr Ala Thr Asp
 1               5                  10                  15

Ser Phe Arg Thr Ala Ser Asp Ala Ser Leu Ala Ser Ser Val Arg
                20                  25                  30

Ser Val Ser Ser Asp Gln Gln Arg Glu Ile Asn Ala Ile Ala Asp Tyr
            35                  40                  45

Leu Thr Asp His Val Phe Ala Ala His Lys Leu Pro Ala Asp Ser
        50                  55                  60

Ala Asp Gly Gln Ala Ala Val Asp Val His Asn Ala Gln Ile Thr Ala
 65                 70                  75                  80

Leu Ile Glu Thr Arg Ala Ser Arg Leu His Phe Glu Gly Thr Pro
                85                  90                  95

Ala Thr Ile Ala Asp Thr Phe Ala Lys Ala Glu Lys Leu Asp Arg Leu
                100                 105                 110

Ala Thr Thr Thr Ser Gly Ala Leu Arg Ala Thr Pro Phe Ala Met Ala
            115                 120                 125

Ser Leu Leu Gln Tyr Met Gln Pro Ala Ile Asn Lys Gly Asp Trp Leu
        130                 135                 140

Pro Ala Pro Leu Lys Pro Leu Thr Pro Leu Ile Ser Gly Ala Leu Ser
145                 150                 155                 160

Gly Ala Met Asp Gln Val Gly Thr Lys Met Met Asp Arg Ala Thr Gly
                165                 170                 175

Asp Leu His Tyr Leu Ser Ala Ser Pro Asp Arg Leu His Asp Ala Met
            180                 185                 190

Ala Ala Ser Val Lys Arg His Ser Pro Ser Leu Ala Arg Gln Val Leu
        195                 200                 205

Asp Thr Gly Val Ala Val Gln Thr Tyr Ser Ala Arg Asn Ala Val Arg
    210                 215                 220

Thr Val Leu Ala Pro Ala Leu Ala Ser Arg Pro Ala Val Gln Gly Ala
225                 230                 235                 240

Val Asp Leu Gly Val Ser Met Ala Gly Gly Leu Ala Ala Asn Ala Gly
                245                 250                 255

Phe Gly Asn Arg Leu Leu Ser Val Gln Ser Arg Asp His Gln Arg Gly
            260                 265                 270

Gly Ala Leu Val Leu Gly Leu Lys Asp Lys Glu Pro Lys Ala Gln Leu
        275                 280                 285

Ser Glu Glu Asn Asp Trp Leu Glu Ala Tyr Lys Ala Ile Lys Ser Ala
290                 295                 300

Ser Tyr Ser Gly Ala Ala Leu Asn Ala Gly Lys Arg Met Ala Gly Leu
305                 310                 315                 320

Pro Leu Asp Met Ala Thr Asp Ala Met Gly Ala Val Arg Ser Leu Val
                325                 330                 335

Ser Ala Ser Ser Leu Thr Gln Asn Gly Leu Ala Leu Ala Gly Gly Phe
            340                 345                 350

Ala Gly Val Gly Lys Leu Gln Glu Met Ala Thr Lys Asn Ile Thr Asp
        355                 360                 365

Pro Ala Thr Lys Ala Ala Val Ser Gln Leu Thr Asn Leu Ala Gly Ser
    370                 375                 380

Ala Ala Val Phe Ala Gly Trp Thr Thr Ala Ala Leu Thr Thr Asp Pro
385                 390                 395                 400
```

```
                                    -continued

Ala Val Lys Lys Ala Glu Ser Phe Ile Gln Asp Thr Val Lys Ser Thr
            405                 410                 415

Ala Ser Ser Thr Thr Gly Tyr Val Ala Asp Gln Thr Val Lys Leu Ala
            420                 425                 430

Lys Thr Val Lys Asp Met Gly Gly Glu Ala Ile Thr His Thr Gly Ala
        435                 440                 445

Ser Leu Arg Asn Thr Val Asn Asn Leu Arg Gln Arg Pro Ala Arg Glu
    450                 455                 460

Ala Asp Ile Glu Glu Gly Gly Thr Ala Ala Ser Pro Ser Glu Ile Pro
465                 470                 475                 480

Phe Arg Pro Met Arg Ser
                485
```

RECOMBINANT CONSTRUCTS AND TECHNIQUES FOR DELIVERING TO EUCARYOTIC CELLS BACTERIAL PROTEINS THAT ARE SECRETED VIA TYPE III SECRETION SYSTEMS

This application claims the benefit of U.S. Provisional Patent Application Ser. No. 60/153,507, filed Sep. 13, 1999.

This invention was made in part with support by the U.S. Government under Grant No. MCB-953034488 from the National Science Foundation. The U.S. Government may have certain rights in this invention.

BACKGROUND OF THE INVENTION

The most common bacterial pathogens of plants colonize the apoplast, and from that location outside of the walls of living cells they incite a variety of diseases in most cultivated plants (Alfano et al., "Bacterial Pathogens in Plants: Life Up Against the Wall," *Plant Cell* 8:1683–1698 (1996)). The majority of these are Gram-negative bacteria in the genera Erwinia, Pseudomonas, Xanthomonas, and Ralstonia. Most are host specific and will elicit the hypersensitive response ("HR") in nonhosts. The HR is a rapid, programmed death of plant cells in contact with the pathogen. Some of the defense responses associated with the HR are localized at the periphery of plant cells at the site of bacterial contact, but what actually stops bacterial growth is not known (Brown et al., "hrp genes in *Xanthomonas campestris* pv. *vesicatoria* Determine Ability to Suppress Papilla Deposition in Pepper Mesophyll Cells," *MPMI* 8:825–836 (1995); Young et al., "Changes in the Plasma Membrane Distribution of Rice Phospholipase D During Resistant Interactions With *Xanthomonas oryzae* pv. *oryzae*," *Plant Cell* 8:1079–1090 (1996); Bestwick et al., "Localization of Hydrogen Peroxide Accumulation During the Hypersensitive Reaction of Lettuce Cells to *Pseudomonas syringae* pv. *phaseolicola*," *Plant Cell* 9:209–221 (1997)). Pathogenesis in host plants, in contrast, involves prolonged bacterial multiplication, spread to surrounding tissues, and the eventual production of macroscopic symptoms characteristic of the disease. Although these bacteria are diverse in their taxonomy and pathology, they all possess hrp ("hypersensitive response and pathogenicity") genes which direct their ability to elicit the HR in nonhosts or to be pathogenic (and parasitic) in hosts (Lindgren, "The Role of hrp Genes During Plant-Bacterial Interactions," *Annu. Rev. Phytopathol.* 35:129–152 (1997)). The hrp genes encode a type III protein secretion system that appears to be capable of delivering proteins, known as effector proteins, across the walls and plasma membranes of living plant cells. Such effector proteins are variously known as hypersensitive response elicitors, Avr (Avirulence) proteins, Hop (hypersensitive response and pathogenicity-dependent outer proteins), Vir (virulence) proteins, or Pth (pathogenicity) proteins, depending on the phenotype by which they were discovered (see, e.g., Alfano et al., "The Type III (Hrp) Secretion Pathway of Plant Pathogenic Bacteria: Trafficking Harpins, Avr Proteins, and Death," *J. Bacteriol.* 179:5655–5662 (1997), which is hereby incorporated by reference). The Avr proteins are so named because they can betray the parasite to the R gene-encoded surveillance system of plants, thereby triggering the HR (Vivian et al., "Avirulence Genes in Plant-Pathogenic Bacteria: Signals or Weapons?," *Microbiology* 143:693–704 (1997); Leach et al., "Bacterial Avirulence Genes," *Annul. Rev. Phytopathol.* 34:153–179 (1996)). But Avr-like proteins also appear to be key to parasitism in compatible host plants, where the parasite proteins are undetected and the HR is not triggered. Thus, bacterial avirulence and pathogenicity are interrelated phenomena and explorations of HR elicitation are furthering our understanding of parasitic mechanisms.

A current model for plant-bacterium interaction and co-evolution based on Hrp delivery of Avr proteins into plant cells proposes that (i) Avr-like proteins are the primary effectors of parasitism, (ii) conserved Hrp systems are capable of delivering many, diverse Avr-like proteins into plant cells, and (iii) genetic changes in host populations that reduce the parasitic benefit of an effector protein or allow its recognition by the R-gene surveillance system will lead to a proliferation of complex arsenals of avr-like genes in co-evolving bacteria (Alfano et al., "Bacterial Pathogens in Plants: Life Up Against the Wall," *Plant Cell*, 8:1683–1698 (1996)). There are still many gaps in this model. For example, the physical transfer of Avr proteins into plant cells has never been observed, the virulence functions of Avr proteins are unknown, and it is likely that previous searches for Avr genes in various bacteria have yielded incomplete inventories of the genes in various bacteria and, thus, incomplete inventories of the genes encoding effector proteins.

Until recently, Avr proteins had not been reported outside of the cytoplasm of living *Pseudomonas syringae* and Xanthomonas spp. cells (Leach et al., "Bacterial Avirulence Genes," *Annul. Rev. Phytopathol,* 34:153–179 (1996); Puri et al., "Expression of avrPphB, an Avirulence Gene from *Pseudomonas Syringae* pv. *phaseolicola*, and the Delivery of Signals Causing the Hypersensitive Reaction in Bean," *MPMI* 10:247–256 (1997)), but it now appears that the Hrp systems of Erwinia spp. can secrete Avr proteins in culture. A homolog of the *Pseudomonas syringae* pv. *tomato* avrE gene has been found in *Erwinia amylovora* and designated dspA in strain CFBP1430 and dspE in strain Ea321 (Gaudriault et al., "DspA, an Essential Pathogenicity Factor of *Erwinia amylovora* Showing Homology with AvrE of *Pseudomonas syringae*, is Secreted via the Hrp Secretion Pathway in a DspB-dependent Way," *Mol. Microbiol.*, 26:1057–1069 (1997); Bogdanove et al., "Homology and Functional Similarity of a hrp-linked Pathogenicity Operon, dspEF, of *Erwinia amylovora* and the avrE locus of *Pseudomonas syringae* Pathovar Tomato," *Proc. Natl. Acad. Sci. USA*, 95:1325–1330 (1998)). dsp genes are required for the pathogenicity of *Erwinia amylovora*, but not for HR elicitation. A protein of the expected size of DspA is secreted in a Hrp- and DspB-dependent manner by CFBP1430 (DspB is a potential chaperone) (Gaudriault et al., "DspA, an Essential Pathogenicity Factor of *Erwinia amylovora* Showing Homology with AvrE of *Pseudomonas syringae*, is Secreted via the Hrp Secretion Pathway in a DspB-dependent Way," *Mol. Microbiol.*, 26:1057–1069 (1997)). Specific antibodies were used to demonstrate unambiguously that DspE is efficiently secreted in a Hrp-dependent manner by strain Ea321 (Bogdanove et al., "*Erwinia amylovora* Secretes DspE, a Pathogenicity Factor and Functional AvrE Homolog, Through the Hrp (Type III Secretion) Pathway," *J. Bacteriol.*, 180(8):2244–2247 (1998)).

Furthermore, the *Erwinia chrysanthemi* Hrp system enables *E. coli* to secrete effector proteins of *P. syringae* and Yersinia spp. (Ham, et al., "A Cloned *Erwinia chrysanthemi* Hrp (Type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA* 95:10206–10211 (1998); Anderson et al., "Reciprocal Secretion of Proteins by the Bacterial Type III Machines of Plant and Animal Pathogens Suggests Universal Recognition of mRNA Targeting Signals," *Proc. Natl. Acad. Sci. USA* 96:12839–12843 (1999); Mudgett and Staskawicz, "Characterization of the *Pseudomonas syringae* pv. *tomato* AvrRpt2 Protein: Demonstration of Secretion and Processing During Bacterial Pathogenesis," *Mol. Microbiol.* 32:927–941 (1999)). Also, conditions have now been defined that permit detection of Hrp-dependent secretion of effector proteins by *P. syringae* and *X. campestris*. Rossier et al., "The Xanthomonas Hrp Type III System Secretes Proteins from Plant and Mammalian Bacterial Pathogens," *Proc. Natl. Acad. Sci. USA* 96:9368–9373 (1999); van Dijk et al., "The Avr (Effector) Proteins HrmA (HopPsyA) and AvrPto are Secreted in Culture from *Pseudomonas syringae* Pathovars via the Hrp (Type III) Protein Secretion System in a Temperature and pH-Sensitive Manner," *J. Bacteriol.* 181:4790–4797 (1999)).

The biochemical activities or parasite-promoting functions of effector proteins remain unclear, although several of those known make measurable contributions to virulence (Leach et al., "Bacterial Avirulence Genes," *Annul. Rev. Phytopathol*, 34:153–179 (1996)). Members of the AvrBs3 family in Xanthomonas spp. are targeted to the plant nucleus (Van den Ackerveken et al., "Bacterial Avirulence Proteins as Triggers of Plant Defense Resistance," *Trends Microbiol,* (1997); Gabriel, "Targeting of Protein Signals from Xanthomonas to the Plant Nucleus," *Trends Plant Sci.,* 2:204–206 (1997)), and some of these have been shown recently to redundantly encode watersoaking functions associated with circulence (Yang et al., "Watersoaking Function(s) of XcmH1005 are Redundantly Encoded by Members of the Xanthomonas avr/pth Gene Family," *MPMI,* 9:105–113 (1996)). AvrD (*Pseudomonas syringae* pv. *tomato*) directs the synthesis of syringolide elicitors of the HR (Leach et al., "Bacterial Avirulence Genes," *Annul. Rev. Phytopathol,* 34:153–179 (1996)); AvrBs2 (*Xanthomonas campestris* pv. *vesicatoria*) shows similarity to *A. tumefaciens* agrocinopine synthase (Swords et al., "Spontaneous and Induced Mutations in a Single Open Reading Frame Alters Both Virulence and Avirulence in *Xanthomonas campestris* pv. *vesicatoria* avrBs2," *J. Bacteriol.,* 4661–4669 (1996)); and AvrRxv (*Xanthomonas campestris* pv. *vesicatoria*) is a homolog of AvrA (*Salmonella typhimurium*) and YopJ (Yersinia spp.), proteins which travel the type III pathway in animal pathogens and trigger apoptosis in macrophages (Hardt et al., "A Secreted Salmonella Protein With Homology to an Avirulence Determinant of Plant Pathogenic Bacteria," *Proc. Natl. Acad. Sci. USA,* 94:9887–9892 (1997); Monack et al., Yersinia Signals Macrophages to Undergo Apoptosis and YopJ is Necessary for this Cell Death," *Proc. Natl. Acad. Sci. USA,* 94:10385–10390 (1997)). This last observation has led to the suggestion that avr-R gene interactions may occur also in animal pathogenesis (Galan, "'Avirulence Gene' in Animal Pathogens?," *Trends Microbiol.,* 6:3–6 (1998)).

The primary sequences of the *Pseudomonas syringae* Avr proteins reveal little about their potential function, but interestingly, when heterologously expressed in plants, three of them have produced necrosis in test plants lacking the cognate R gene (Gopalan et al., "Expression of the *Pseudomonas syringae* Avirulence Protein AvrB in Plant Cells Alleviates its Dependence on the Hypersensitive Response and Pathogenicity (Hrp) Secretion System in Eliciting Genotype-specific Hypersensitive Cell Death," *Plant Cell,* 8:1095–1105 (1996); Stevens et al., "Sequence Variations in Alleles of the Avirulence Gene avrPphE.R2 from *Pseudomonas syringae* pv. *phaseolicola* Lead to Loss of Recognition of the AvrPphE Protein Within Bean Cells and Gain in Cultivar Specific Virulence," *Mol. Microbiol.,* 29(1):165–77 (1998); McNellis et al., "Glucocorticoid-inducible Expression of a Bacterial Avirulence Gene in Transgenic Arabidopsis Induces Hypersensitive Cell Death," *Plant J.,* 14(2):247–57 (1998)). A key question is whether this results from interaction of abnormally high levels of the bacterial protein with plant virulence targets or with cross-reacting R-gene products. Further evidence suggesting that some avr genes in *Pseudomonas syringae* are beneficial to the bacteria in host plants is found in recent studies of avrD and avrPphE. Highly conserved, nonfunctional alleles of these genes have been retained in pathogens whose hosts would recognize the functional Avr product (Stevens et al., "Sequence Variations in Alleles of the Avirulence Gene avrPphE.R2 from *Pseudomonas syringae* pv. *phaseolicola* Lead to Loss of Recognition of the AvrPphE Protein Within Bean Cells and Gain in Cultivar Specific Virulence," *Mol. Microbiol.,* 29(1):165–77 (1998); Keith et al., "Comparison of avrD Alleles from *Pseudomonas syringae* pv. *glycinea,*" *MPMI,* 10:416–422 (1997)).

Avr-like genes may function heterologously to support pathogenesis as well as HR elicitation. The pathogenicity of an *Erwinia amylovora* dspE mutant can be restored (at least partially) by a plasmid carrying the *Pseudomonas syringae* avrE locus, suggesting that DspE and AvrE have similar functions (Bogdanove et al., "Homology and Functional Similarity of a hrp-linked Pathogenicity Operon, dspEF, of *Erwinia amylovora* and the avrE locus of *Pseudomonas syringae* Pathovar Tomato," *Proc. Natl. Acad. Sci. USA,* 95:1325–1330 (1998)). That dspE is essential for *Erwinia amylovora* pathogenicity, whereas avrE contributes only quantitatively to the virulence of *Pseudomonas syringae* pv tomato (Lorang et al., "avrA and avrE in *Pseudomonas syringae* pv. *Tomato* PT23 Play a Role in Virulence on Tomato Plants," *MPMI,* 7:508–515 (1994)), suggests that there is less redundancy in the *Erwinia amylovora* virulence system. This would be consistent with a more recent acquisition of the Hrp system by *Erwinia amylovora* and/or a slower coevolution with its perennial hosts (Bogdanove et al., "Homology and Functional Similarity of a hrp-linked Pathogenicity Operon, dspEF, of *Erwinia amylovora* and the avrE locus of *Pseudomonas syringae* Pathovar Tomato," *Proc. Natl. Acad. Sci. USA,* 95:1325–1330 (1998)). The heterologous function of *Pseudomonas syringae* avr genes in *Erwinia amylovora* and *Erwinia chrysanthemi* suggests that Hrp+ bacteria in the field may be able to 'sample' a buffet of avr-like genes from diverse sources in their coevolution with changing plant populations. Many avr genes have been known to be potentially mobile, because of their presence on plasmids (Vivian et al., "Avirulence Genes in Plant-Pathogenic Bacteria: Signals or Weapons?," *Microbiology* 143:693–704 (1997); Leach et al., "Bacterial Avirulence Genes," *Annu. Rev. Phytopathol,* 34:153–179 (1996)). Recent observations with *Pseudomonas syringae* highlight the apparent mobility of avr genes. Several *Pseudomonas syringae* avr genes are liked with transposable elements or phage sequences (Hanekamp et al., "Avirulence Gene D of *Pseudomonas syringae* pv. *Tomato* May Have Undergone Horizontal Gene Transfer," *FEBS Lett.,* 415:40–44 (1997)), and the hrp clusters in different strains of *Pseudomonas syringae,* although conserved in themselves, are bordered by a hypervariable region enriched in avr genes and mobile DNA elements. Alfano et al., "The *Pseudomonas syringae* Hrp Pathogenicity Island has a Tripartite Mosaic Structure Composed of a Cluster of Type III Secretion Genes Bounded by Exchangeable Effector and Conserved Effector Loci that Contribute to Parasitic Fitness and Pathogenicity in Plants," *Proc. Natl. Acad. Sci. USA* 97:4856–4861 (2000).

Two classes of extracellular Hrp proteins have now been defined-harpins and pilins. Harpins are glycine-rich proteins that lack cysteine, are secreted in culture when the Hrp system is expressed, and possess heat-stable HR elicitor activity when infiltrated into the leaves of tobacco and several other plants (Alfano et al., "Bacterial Pathogens in Plants: Life Up Against the Wall," *Plant Cell,* 8:1683–1698 (1996)). Mutation of the prototypical hrpN harpin gene in *Erwinia amylovora* Ea321 strongly diminishes HR and pathogenicity phenotypes (Kim et al., "HrpW of *Erwinia amylovora,* a New Harpin That is a Member of a Proposed Class of Pectate Lyases," *J. Bacteriol.* 180(19):5203–5210 (1998)), but mutation of the hrpZ harpin gene in different *Pseudomonas syringae* strains has little or no effect on Hrp phenotypes (Alfano et al., "Analysis of the Role of the *Pseudomonas syringae* pv. *syringae* HrpZ Harpin in Elicitation of the Hypersensitive Response in Tobacco Using Functionally Nonpolar Deletion Mutations, Truncated HrpZ Fragments, and hrmA Mutations," *Mol. Microbiol.* 19:715–728 (1996); Charkowski et al.,. "The *Pseudomonas syringae* pv. *tomato* HrpW Protein Has Domains Similar to Harpins and Pectate Lyases and Can Elicit the Plant Hypersensitive Response and Bind to Pectate," *J. Bacteriol.* 180 (19):5211–5217 (1998)). The natural function of harpins or the basis for their ability to elicit an apparent programmed cell death when artificially introduced into the apoplast of plants is unknown. However, two lines of evidence point to a site of action in the plant cell wall. First, purified *Pseudomonas syringae* harpin binds to cell walls and has biological activity only with walled cells (Hoyos et al., "The Interaction of Harpin$_{Pss}$ With Plant Cell Walls," *MPMI* 9:608–616 (1996)). Second, HrpW, a second harpin discovered in both *Erwinia amylovora* and *Pseudomonas syringae,* has an N-terminal half that is harpin-like but a C-terminal half that is homologous to a newly-defined class of pectate lyases found in fungal and bacterial pathogens (Kim et al., "HrpW of *Erwinia amylovora,* a New Harpin That is a Member of a Proposed Class of Pectate Lyases," *J. Bacteriol.* 180(19):5203–5210 (1998); Charkowski et al., "The *Pseudomonas syringae* pv. *tomato* HrpW Protein Has Domains Similar to Harpins and Pectate Lyases and Can Elicit the Plant Hypersensitive Response and Bind to Pectate," *J. Bacteriol.* 180 (19):5211–5217 (1998)). Elicitor activity resides in the harpin domain, and the pectate lyase domain, although lacking enzymatic activity, binds specifically to pectate (Charkowski, A. et al., "The *Pseudomonas syringae* pv. *tomato* HrpW Protein Has Domains Similar to Harpins and Pectate Lyases and Can Elicit the Plant Hypersensitive Response and Bind to Pectate," *J. Bacteriol.* 180 (19):5211–5217 (1998)). The second class of extracellular Hrp proteins are represented by the *Pseudomonas syringae* HrpA pilin, which is a subunit of a Hrp-pilus that is 6–8 nm in diameter and is formed on bacteria in a Hrp-dependent manner (Roine et al., "Hrp Pilus: An hrp-dependent Bacterial Surface Appendage Produced by *Pseudomonas syringae* pv. *tomato* DC3000, " *Proc. Natl. Acad. Sci. USA* 94:3459–3464 (1997)). The Hrp pilus is required for pathogenicity and elicitation of the HR, and a similar structure is important for T-DNA transfer in *Agrobacterium tumefaciens* (Fullner et al., "Pilus Assembly by Agrobacterium T-DNA Transfer Genes," *Science,* 237:1107–1109 (1996)). Whether these structures promote the transfer of bacterial macromolecules into plant cells by serving as conduits, guides, or attachment factors is not known.

Type III secretion systems are present in both animal and plant pathogenic bacteria, which indicates that they are capable of operating not only across bacterial genera but also across host kingdoms (Galan et al., "Type III Secretion Machines: Bacterial Devices for Protein Delivery into Host Cells," *Science* 284:1322–1328 (1999)). At present, the metabolic changes caused by effector proteins secreted by the type III protein secretion system of plant pathogenic bacteria are unknown. However, perturbations in pathways involved in innate immunity, programmed cell death, and the cell cycle are unlikely. Supporting this expectation is the finding that effectors of Salmonella, Shigella, and Yersinia spp. have activities such as altering F-actin stability, activation of caspase-1, tyrosine phosphatase activity, and inhibition of mitogen-activated protein kinases (Galán et al., "Type III Secretion Machines: Ingenious Bacterial Devices for Protein Delivery into Host Cells," *Science* 284:1322–1328 (1999); Orth et al., "Inhibition of the Mitogen-Activated Protein Kinase Superfamily by a Yersinia Effector," *Science* 285:1920–1923 (1999)). Many of the metabolic targets are likely to be universal among eucaryotes and, therefore, these phytopathogen effector proteins are likely to provide tools for altering the metabolism of yeast, nematodes, insects, and higher animals for various biotechnological purposes.

A limiting factor in the potential biotechnological use of these phytopathogen effector proteins is that the metabolic targets of the effector proteins are inside host cells and, therefore, the effector proteins must be either produced inside the target cells or delivered into them by some means. One such means is gene therapy techniques, however, this technology is relatively difficult to apply.

Thus, it would be beneficial to obtain a recombinant construct and delivery system which overcomes these and other deficiencies in the art.

SUMMARY OF THE INVENTION

One aspect of the present invention relates to a method for delivering effector proteins into a target cell. This method involves introducing into the target cell an effector protein fused to a protein transduction domain of a human immunodeficiency virus TAT protein or derivatives or functional analogs thereof.

Another aspect of the present invention relates to a DNA construct including a first DNA molecule encoding an effector protein and a second DNA molecule operatively associated with the first DNA molecule and encoding a protein transduction domain of a human immunodeficiency virus TAT protein or derivatives or functional analogs thereof.

The method of the present invention allows efficient delivery of effector proteins into cells, in particular, mammalian cells. This method also allows for delivery of effector proteins for use in pharmaceutical, insecticide, fungicide, herbicide, and other applications. In particular, the present invention will allow the delivery of effector proteins into patients in the form of protein therapy. Therapy with biologically active full-length proteins will allow access to the built-in evolutionary specificity of these proteins for their targets, thereby potentially avoiding the nonspecific effects sometimes seen with small-molecule therapies. Moreover, when used in conjunction with tissue-specific viral vectors, use of the present invention allows the targeted delivery of effector proteins to particular cells with the added benefit of secondary redistribution of the effector protein subsequent to the initial targeting. A precedent for this approach can be found in an experiment wherein the VP22 protein transduction domain was fused to the p53 tumor suppressor protein (Phelan et al., "Intercellular Delivery of Functional p53 by the Herpesvirus Protein VP22," *Nat. Biotechnol.* 16:440–443 (1998), which is hereby incorporated by reference).

DETAILED DESCRIPTION OF THE INVENTION

One aspect of the present invention relates to a method for delivering effector proteins into a target cell. This method involves introducing into the target cell an effector protein fused to a protein transduction domain of a human immunodeficiency virus TAT protein or derivatives or functional analogs thereof.

Effector proteins are delivered into host cells via the type III protein secretion system. Thus, effector proteins for the present invention can be obtained with constructs utilizing a DNA molecule encoding a functional type III secretion system and a DNA molecule encoding a protein or polypeptide capable of being secreted by the type III secretion system, as disclosed in the U.S. patent application Ser. No. 09/350,852, filed Jul. 9, 1999, which is hereby incorporated by reference. These constructs can be used under conditions effective to transform host cells so that they express and secrete (i.e., into the host cell environment) an effector protein or polypeptide of interest, which is then isolated. Effective conditions include optimal growth temperatures and nutrient media which will enable maximum growth of the host cells and maximal expression of the protein or polypeptide of interest. Exemplary culture media include, without limitation, LM media and minimal media, both of which are known in the art. One of ordinary skill in the art can readily determine the optimal growth temperatures for particular strains of host cells and suitable nutrient media capable of optimizing host cell growth.

Figure 1:
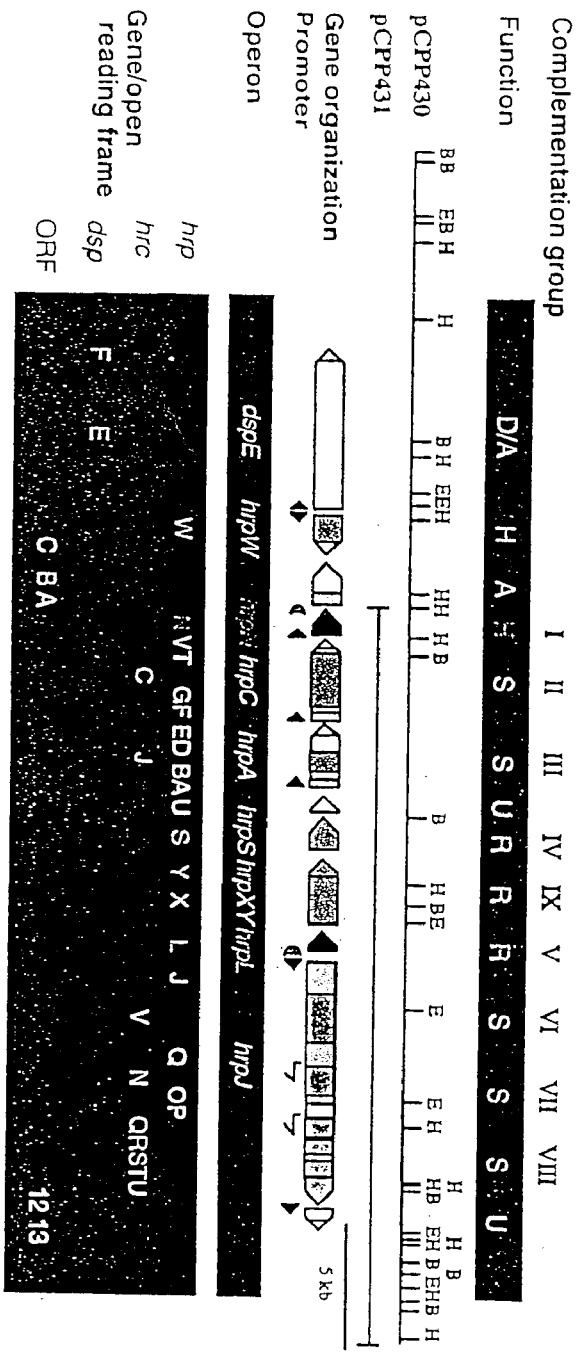
FIG. 1 is a diagram showing the genetic organization of the hrp and dsp genes contained by cosmids pCPP430 and pCPP431. The letters designating the known or proposed functions correspond to the following: S, secretion; R, regulation; H, harpin; A, avirulence; D, disease; U, unknown.
Figure 2:
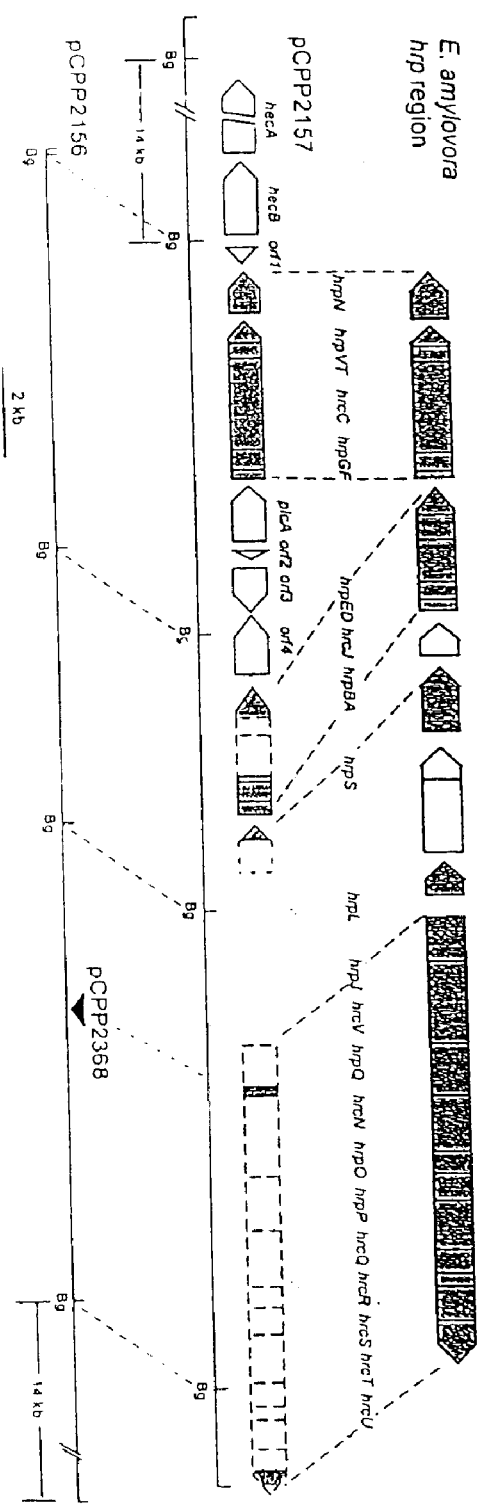
FIG. 2 is a diagram of the physical maps for cosmids pCPP2156 and pCPP2157, which contain the *Erwinia chrysanthemi* hrp region, and comparison of the hrp regions of *Erwinia chrysanthemi* and *Erwinia amylovora* (Bauer et al., "*Erwinia chrysanthemi* harpin$_{Ech}$: An Elicitor of the Hypersensitive Response that Contributes to Soft-rot Pathogenesis," *MPMI* 8:484–491 (1995); Kim et al., "The hrpC and hrpN Operons of *Erwinia chrysanthemi* EC 16 are Flanked by plcA and Homologs of Hemolysin/Adhesin Genes and Accompanying Activator/Transporter Genes," *MPMI* 11(6):563–567 (1998); Bogdanove et al., "*Erwinia amylovora* Secretes Harpin via a Type III of Pathway and Contains a Homolog of YopN of Yersinia spp.," *J. Bacteriol.* 178:1720–1730 (1996); Wei et al., "Harpin, Elicitor of the Hypersensitive Response Produced by the Plant Pathogen *Erwinia amylovora,*" *Science,* 257:85–88 (1992); Wei et al., "HrpI of *Erwinia amylovora* Functions in Secretion of Harpin and is a Member of a New Protein Family," *J. Bacteriol.,* 175:7958–7967 (1993); Kim et al., "The HrpA and HrpC Operons of *Erwinia amylovora* Encode Components of a Type III Pathway that Secrets Harpin," *J. Bacteriol.* 179:1690–1697 (1997), which are hereby incorporated by reference). Arrow-shaped boxes denote putative transcriptional units. Shadowed areas denote hrp regions. Dashed boxes denote transcriptional units predicted on the basis of the homology and spacing of partially sequenced regions (shaded areas) in comparison with the corresponding *Erwinia amylovora* hrp genes. The filled triangle indicates the location of mini-Tn5Cm in pCPP2368.

Suitable type III secretion systems include those obtained from the genus Erwinia, more preferably, the harpin secretion systems obtained from *Erwinia amylovora* or *Erwinia chrysanthemi,* and Pseudomonas, more preferably, the harpin secretion systems obtained from *Pseudomonas syringae*. For example, the harpin secretion system of *Erwinia amylovora* is present on cosmid pCPP430 (Beer et al., "The hrp Gene Cluster of *Erwinia amylovora,*" in *Advances in Molecular Genetics of plant-Microbe Interactions,* Proceedings of the 5th International Symposium on the Molecular Genetics of Plant-Microbe Interactions, Interlaken, Switzerland, September, 1990, pp. 53–60 (1991) which is hereby incorporated by reference) and the harpin secretion system of *Erwinia carotovora* is present in cosmid pCPP2156 (Ham et al., "A Cloned *Erwinia chrysanthemi* Hrp (type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA,* 95(17): 10206–11 (1998), which is hereby incorporated by reference). A diagram of cosmid pCPP430 is shown at FIG. 1 and a diagram of cosmid pCPP2156 is shown at FIG. 2.

Type III protein secretion systems are present in bacterial pathogens of both animals and plants, and are typified by the type III system of Yersinia spp. (Finlay et al., "Common Themes in Microbial Pathogenicity Revisited," *Microbiol. Mol. Biol. Rev.,* 61:136–169 (1997); Cornelis et al., "The Yersinia Yop Regulon: A Bacterial System for Subverting Eukaryotic Cells," *Mol. Microbiol.,* 23:861–867 (1997), which are hereby incorporated by reference). These animal pathogens are primarily extracellular parasites, and their Yops (Yersinia outer proteins) are secreted and translocated directly into host cells in a contact-dependent manner (Cornelis et al., "The Yersinia Yop Regulon: A Bacterial System for Subverting Eukaryotic Cells," *Mol. Microbiol.,* 23:861–867 (1997), which is hereby incorporated by reference). A similar host-contact dependency may operate in most plant pathogenic bacteria. Nine of the hrp genes are universal components of type III secretion systems, and these have been renamed hrc (HR and conserved) and given the last-letter designation of their Yersinia homolog (with the exception of hrcV) (Bogdanove et al., "Unified Nomenclature for Broadly Conserved hrp Genes of Phytopathogenic Bacteria," *Mol. Microbiol.,* 20:681–683 (1996), which is hereby incorporated by reference). The Hrc proteins enable protein movement across the bacterial inner and outer membranes independently of the general protein export (Sec) pathway (Charkowski et al., "Altered Localization of HrpZ in *Pseudomonas syringae* pv. *syringae* hrp Mutants Suggests That Different Components of the Type III Secretion Pathway Control Protein Translocation Across the Inner and Outer Membranes of Gram-negative Bacteria," *J. Bacteriol.,* 179:3866–3874 (1997), which is hereby incorporated by reference). In contrast to the Hrc proteins, the Hrp proteins may be peripheral components of the Hrp secretion system and are more likely to perform type III secretion functions that are extracellular and specific to protein transfer across the plant cell wall and plasma membrane.

The effector protein or polypeptide must be compatible for secretion by the type III secretion system employed. By compatible, it is intended that the protein or polypeptide contain a secretion signal that can be recognized by the particular type III secretion system that is employed. The secretion signal enables the expressed protein or polypeptide to be recognized by the type III secretion system and transported via the expressed secretion system into the extracellular environment in which the recombinant host cells exist, i.e., culture medium.

Suitable secretion signals can be either an mRNA or a polypeptide fragment of a naturally-occurring protein secreted by the type III secretion system.

Compatible secretion signals can readily be determined for any particular type III secretion system that is to be employed. By identifying proteins that are normally secreted by the type III secretion system, it is possible to prepare deletion mutants missing various fragments of the full length protein that is normally secreted by the secretion system. Using labeled antibodies raised against epitopes of the various deletion fragments that are expressed (i.e., N-terminal epitopes, C-terminal epitopes, etc.), it is possible to identify deletion mutants that are secreted and those that are not secreted. Thus, protein domains necessary for secretion of the full length protein can be readily identified. Once the protein domains have been identified and sequenced, they can be utilized as secretion signals in fusion proteins of the present invention.

Typically, the secretion signal is an N-terminal domain of a protein that is normally secreted by the particular type III secretion system, for example, a 201 amino acid sequence from the N-terminal domain of the DspE protein of *Erwinia amylovora* (see, e.g., U.S. patent application Ser. No. 09/350,852, filed Jul. 9, 1999, which is hereby incorporated by reference). The 201 amino acid secretion signal of *Erwinia amylovora* DspE is compatible with the harpin secretion system of *Erwinia amylovora*. Other secretion signals that are compatible with various type III secretion systems have been described in the art and others are continually being identified.

Purified effector protein may be obtained by several methods. The protein or polypeptide is preferably produced in purified form (preferably at least about 80%, more preferably 90%, pure) by conventional techniques. Since the recombinant host cells express a type III secretion system, the protein or polypeptide is secreted into the growth medium of recombinant host cells. In such cases, to isolate the protein, the recombinant host cells are propagated, the growth medium is centrifuged to separate cellular components from supernatant containing the secreted protein or polypeptide, and the supernatant is removed. The supernatant is then subjected to sequential ammonium sulfate precipitation. The fraction containing the polypeptide or protein is subjected to gel filtration in an appropriately sized dextran or polyacrylamide column to separate the proteins. If necessary, the protein fraction may be further purified by HPLC.

Effector proteins carrying protein transduction domains may also be prepared independently of the type III secretion system by using current state-of-the-art techniques for preparing large amounts of purified proteins from recombinant *E. coli* cells. Such techniques employ strong, inducible promoters and peptide tags, such as $His_6$, for one-step affinity purification of the recombinant protein from *E. coli* cell lysates (as described below in Example 1).

In one embodiment, the target cell is a eucaryote cell. The eucaryote cells include those in tissue culture, such as HeLa cells, or in whole animals, such as those delivered to mouse via intraperitoneal injection (Schwarze et al., "Protein Transduction: Unrestricted Delivery into all Cells?" *Trends Cell Biol.* 10:290–295 (2000), which is hereby incorporated by reference).

The effector protein may be produced by a bacterial plant pathogen, animal pathogen, or a rhizosphere bacteria, including, but not limited to enteropathogenic *Escherichia coli, Salmonella typhimurium,* Shigella spp., Yersinia spp., *Pseudomonas syringae, Xanthomonas campestris, Ralstonia solanacearum, Erwinia amylovora, Pseudomonas fluorescens,* and *Pseudomonas aeruginosa.*

Suitable effector proteins include a hypersensitive response elicitor, an avirulence protein, a hypersensitive response and pathogenicity-dependent outer protein, a virulence protein, and a pathogenicity protein. Examples of effector proteins include HopPsyA AAF71481 (*P. syringae*), HopPtoA AF232006 (*P. syringae*), Tir BAA96815 (*E. coli*), ExoS AAG07228 (*P. aeruginosa*), ExoT AAG03434 (*P. aeruginosa*), ExoY AAG05579 (*P. aeruginosa*), SopE AAC02071 (*S. typhimurium*), SopB AAF21057 (SigA) (*S. typhimurium*), SipA CAA63302 (*S. typhimurium*), SptP AAC44349 (*S. typhimurium*), IpaB A34965 (Shigella spp.), IpaA AAA26525 (Shigella spp.), IpaD S15579 (Shigella spp.), YopE S14242 (Yersinia spp.), YopH AAC69768 (Yersinia spp.), YpkA AAC69765 (Yersinia spp.), YopJ AAC69766 (YopP) (Yersinia spp.), AvrPto AAA25728 (*P. syringae*), AvrBs2 AAD11434 (*X. campestris*), and AvrBs3 CAA34257 (*X. campestris*) (see, e.g., Galán et al., "Type III Secretion Machines: Bacterial Devices for Protein Delivery into Host Cells," *Science* 284:1322–1328 (1999), which is hereby incorporated by reference).

In one embodiment, the effector protein is heterologous (i.e., not normally present) to the target cell.

In the present invention, the effector protein is fused to a protein transduction domain (PTD) of a human immunodeficiency virus (HIV) trans-activating protein (TAT) protein or derivatives or functional analogs thereof to produce a fusion protein. The protein transduction domain of a human immunodeficiency virus TAT protein has the following amino acid sequence YGRKKRRQRRR (SEQ. ID. No. 1) (Schwarze et al., "In Vivo Protein Transduction: Delivery of a Biologically Active Protein into the Mouse," *Science* 285:1569–1572 (1999); Strauss, "Introducing Proteins Into the Body's Cells," *Science* 285:466–467 (1999), which are hereby incorporated by reference). Functional analogous protein transduction domains are also found in the herpes-simplex-virus-1 DNA-binding protein VP22 and the Drosophila Antennapedia (Antp) homeotic transcription factor (Joliot et al., "Antennapedia Homeobox Peptide Regulates Neural Morphogenesis," *Proc. Natl. Acad. Sci. USA* 88:1864–1868 (1991); Elliott, et al., "Intercellular Trafficking and Protein Delivery by a Herpesvirus Structural Protein," *Cell* 88:223–233 (1997), which are hereby incorporated by reference). A common factor in these protein transduction domains is the presence of the basic amino acids Arg and Lys. Research in several laboratories around the world is directed at identifying additional proteins with protein transduction domains and identifying variants of known protein transduction domains with improved protein transduction activity (Schwarze et al., "Protein Transduction: Unrestricted Delivery Into All Cells?," *Trends Cell Biol.* 10:290–295 (2000), which is hereby incorporated by reference).

The fusion proteins of the present invention can be created by standard rDNA techniques. In particular, the effector protein may be linked to PTD from the human immunodeficiency virus TAT protein, whether a mRNA or a polypeptide fragment, by an in-frame gene fusion, which preferably results in linking the mRNA or polypeptide fragment to the N-terminal end of the effector protein. Such fusion proteins include a PTD from the HIV TAT protein linked to an effector protein, for example, by a peptide bond between the PTD from the HIV TAT protein and the effector protein. Fusion proteins can be prepared by ligating two or more DNA molecules together, one of which encodes the effector protein and the other of which encodes the PTD from the HIV TAT protein. The two DNA molecules must be ligated in a manner which allows their proper expressions. A number of efficient expression schemes for preparing fusion proteins have been developed and are well known in the art.

Methods for producing fusion proteins of the present invention are known in the art and are described in, for example, Schwarze et al., "Protein Transduction: Unrestricted Delivery Into All Cells?," *Trends in Cell Biology* 10:290–295 (2000), which is hereby incorporated by reference.

In one embodiment, the effector protein fused to a protein transduction domain of a human immunodeficiency virus TAT protein or derivatives or functional analogs thereof is introduced into the largest cell by topical application.

In another embodiment, the effector protein fused to a protein transduction domain of a human immunodeficiency virus TAT protein or derivatives or functional analogs thereof is introduced by introducing into the target cell a DNA construct which includes a DNA molecule encoding an effector protein operatively associated with a DNA molecule encoding a protein transduction domain of a human immunodeficiency virus TAT protein or derivatives or functional analogs thereof under conditions effective to express the DNA molecule encoding an effector protein in the target cell. This embodiment allows the delivery of the effector protein fused to a protein transduction domain of a human immunodeficiency virus TAT protein to be targeted to particular cells, depending upon the expression system used to deliver the DNA construct. In addition, this embodiment allows secondary redistribution of the effector protein subsequent to the initial targeting.

Once the DNA construct is obtained, it can be incorporated in cells using conventional recombinant DNA technology. Generally, this involves inserting the DNA construct into an expression system to which the DNA construct is heterologous (i.e., not normally present). Expression systems of the present invention contain an expression vector into which is inserted one or more heterologous DNA constructs of the present invention. The heterologous DNA construct is inserted into the expression system or vector in proper sense orientation. The vector contains the necessary elements for the transcription of the DNA constructs of the present invention.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant or engineered genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology,* vol. 185 (1990), which is hereby incorporated by reference), and any derivatives thereof. Suitable vectors are continually being developed and identified. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual,* Cold Springs Laboratory, Cold Springs Harbor, N.Y. (1982), which is hereby incorporated by reference.

A variety of host-vector systems may be utilized to express the effector protein fused to the PTD of the HIV TAT protein. Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. Efficient translation of mRNA in procaryotes requires a ribosome binding site called the Shine-Dalgarno ("SD") sequence on the mRNA. This sequence is a short nucleotide sequence of mRNA that is located before the start codon, usually ATG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. Thus, any SD-ATG combination that can be utilized by host cell ribosomes may be employed. Such combinations include, but are not limited to, SD-ATG combinations synthesized by recombinant techniques, the SD-ATG combination from the cro gene or the N gene of coliphage lambda, or from the *Escherichia coli* tryptophan E, D, C, B or A genes. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned DNA construct of the present invention, it is desirable to use strong promoters in order to obtain a high level of transcription and, hence, expression of the DNA construct. Depending upon the host cell system utilized, any one of a number of suitable promoters may be used. For instance, when cloning in *Escherichia coli*, its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *Escherichia coli* promoters produced by recombinant DNA or other synthetic DNA techniques may be used to provide for transcription of the inserted construct.

Expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

The present invention also relates to a DNA construct including a first DNA molecule encoding an effector protein and a second DNA molecule operatively associated with the first DNA molecule and encoding a protein transduction domain of a human immunodeficiency virus TAT protein or derivatives or functional analogs thereof.

The present invention allows the delivery of effector proteins into patients in the form of protein therapy. Therapy with biologically active full-length proteins will allow access to the built-in evolutionary specificity of these proteins for their targets, thereby potentially avoiding the nonspecific effects sometimes seen with small molecule therapies.

Techniques for delivery of effector proteins into patients in the form of protein therapy are described in Schwartz et al., "Protein Transduction: Unrestricted Delivery Into All Cells?," *Trends in Cell Biology* 10:290–295 (2000), which is hereby incorporated by reference. They can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the fusion protein of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The fusion protein of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the fusion protein of the present invention in solution or suspension may be packaged in a pressurized aerosol container together with suitable propellants, for example, hydrocarbon propellants like propane, butane, or isobutane with conventional adjuvants. The fusion proteins of the present invention also may be administered in a non-pressurized form such as in a nebulizer or atomizer.

EXAMPLES

Example 1

Construction of pCPP3122 (pDF4) (pET16B derivative): A Vector Containing a HIS6-tag and the TAT Protein Transduction Domain (PTD)

To create His6-TAT-effector protein fusions, pET16B (Novagen, Madison, Wis.) was digested with NdeI and NcoI to remove the existing HIS-tag and Factor Xa protease cleavage regions, giving the following sequence (SEQ. ID. No. 2):

```
       NcoI                                                              NdeI
       CCATGGCCATCATCATCATCATCATCATCATCATCACAGCAGCGGCCATATCGAAGGTCGTCATATG
```

The corresponding amino acid sequence is MGHHHHHH-HHHHSSGHIEGRHM (SEQ. ID. No. 3) (HHHHHHHHHH is HIS-Tag).

This digested vector was gel purified on a 1% agarose gel to separate the vector backbone from the sequence illustrated above. The vector backbone fragment was eluted from the gel matrix using the Bio-Rad (Hercules, Calif.) prep-a-gene kit. This purified fragment was ligated to a fragment containing NcoI and NdeI sticky ends that was prepared as follows. To generate an oligonucleotide containing NcoI and NdeI and the nucleotide sequence (SEQ. ID. No. 4):

```
               NcoI                                                          NdeI
            CCATGGGCCATCACCATCACCATCACGGCTATGGCCGTAAAAAACGCCGTCAGCGCCGTCGCGGTCATATG
``` with the corresponding amino acid sequence (SEQ. ID. No. 5):

```
                    MGHHHHHHGYGRKKRRQRRRGHM
                     HIS-Tag  PTD domain
``` four oligonucleotides were synthesized by IDT Inc. (Coralville, Iowa) with the sequences:

```
                         NcoI                              EaeI
pET16b-His6T GGATCACCATGGGCCATCACCATCACCATCACGGCTATGGCCGTAGTCG (SEQ. ID. No.6)

NcoI                              EaeI
pET16b-His6B CGACTACGGCCATAGCCGTGATGGTGATGGTGATGGCCCATGGTGATCC (SEQ. ID. No.7)

EaeI                              NdeI
pET16b-TatT CGGCTATGGCCGTAAAAAACGCCGTCAGCGCCGTCGCGGTCATATGTTACTAGC
(SEQ. ID. No.8)

EaeI                              NdeI
pET16b-TatB GCTAGTAACATATGACCGCGACGGCGCTGACGGCGTTTTTTACGGCCATAGCCG
(SEQ. ID. No.9)
```

These 2 sets of oligonucleotides were annealed, digested with EaeI, and ligated together to create:

```
         NcoI                              EaeI                              NdeI
GGATCACCATGGGCCATCACCATCACCATCACGGCTATGGCCGTAAAAAACGCCGTCAGCGCCGTCGCGGTCATATGTTACTAGC

CCTAGTGGTACCCGGTAGTGGTAGTGGTAGTGCCGATACCGGCATTTTTTGCGGCAGTCGCGGCAGCGCCAGTATACAATGATCG
(SEQ. ID. No.10)
```

The larger fragment was digested with NcoI and NdeI and was separated from the smaller fragments by passage through a G25 spin column (Pharmacia, Piscataway, N.J.). This final construct was ligated to the former pET16B vector backbone. After overnight ligation at 16° C., half the ligation mix was transformed into *E. coli* DH5α (SupE44 ΔlacU169 (f80 lacZΔM15) hsdR17 recA1 endA1 gyrA96 thi-1, available from Life Technologies, Grand Island, N.Y.) via heat-shock transformation. Colonies were selected on LB+Amp plates.

Several individual colonies were cultured and the DNA was harvested and sequenced. A clone containing the desired sequence was obtained and frozen at 80° C.

To create a better multiple cloning site and to obtain a transcription terminator, maintaining flexibility with an existing pFLAG-CTC cloning system, an NdeI-SSPI fragment was cloned from pFLAG-CTC (for construction of C-terminal fusion to FLAG peptide, Ap$^r$, available from Kodak Scientific Imaging Systems, Rochester, N.Y.). This construct was verified via restriction enzyme digests.

A key advantage of pCPP3122 is that it facilitates rapid generation of fusion proteins from effector genes originally cloned in pFLAG-CTC. The latter vector is used to demonstrate that candidate effector proteins are secreted by the type III secretion system.

Example 2

Construction of pCPP3122 Derivatives Expressing Fusions Proteins Including Two Different Effector Proteins hopPsyA encodes the HopPsyA (HrmA) protein of *Pseudomonas syringae* pv. *syringae* 61, and has the following sequence (SEQ. ID. No. 11):
GTGAACCCTATCCATGCACGCTTCTCCAGCG-
TAGAAGCGCTCAGACATTCAAACGTTGATAT-
TCAGGCAATCAAATCCGAGGGTCAGTTGGAAGT-
CAACGGCAAGCGTTACGAGATTCGTGCGGCCGC-
TGACGGCTCAATCGCGGTCCTCAGACCCGATCA-
ACAGTCCAAAGCAGACAAGTTCTTCAAAGGCG-
C AGCGCATCTTATTGGCGGACAAAGCCAGCGTG-
CCCAAATAGCCCAGGTACTCAACGAGAAAGC-
GGCGGCAGTTCCACGCCTGGACAGAATGTTGGG-
CAGACGCTTCGATCTGGAGAAGGGCGGAA-
GTAGCGCTGTGGGCGCCGCAATCAAGGCT-
GCCGACAGCCGACTGACATCAAAACAGACATTT-
GCCAGCTTCCAGCAATGGGCTGAAAAAGCT-
GAGGCGCTCGGGCGATACCGAAATCGGTATCTA-
CATGATCTACAAGAGGGACACGCCAGACA-
CAACGCCTATGAATGCGGCAGAGTCAAGAACAT-
TACCTGGAAACGCTACAGGCTCTCGATAACAA-
GAAAAACCTTATCATACGCCCCGCAGATCC-
ATGATGATCGGGAAGAGGAAGAGCTTGATC-
TGGGCCGATACATCGCTGAAGACAGAAAT-
GCCAGAACCGGCTTTTTTAGAATGGTTCCTAAA-
GACCAACGCGCACCTGAGACAAACTCGGGACG-
ACTTACCATTGGTGTAGAACCTAAATATG-
GAGCGCAGTTGGCCCTCGCAATGGCAACCCTGA-
TGGACAAGCACAAATCTGTGACACAAGGTAAA-
GTCGTCGGTCCGGCAAAATATGGCCAGCAAA-
CTGACTCTGCCATTCTTTACATAAATGGTGATCT-
TGCAAAAGCAGTAAAACTGGGCGAAAAGCT-
GAAAAAGCTGAGCGGTATCCCTCCTGAAGGAT-
TCGTCGAACATACACCGCTAAGCATGCAG-
TCGACGGGTCTCGGTCTTTCTTATGCCGAGTCG-
GTTGAAGGGCAGCCTTCCAGCCACGGACAGGC-
GAGAACACACGTTATCATGGATGCCTTGAAAGG-
CCAGGGCCCCATGGAGAACAGACTCAAAATG-
GCGCTGGCAGAAAGAGGCTATGACCCG-
GAAAATCCGGCGCTCAGGGCGCGAAACTGA
(1128)

HopPsyA has an amino acid sequence (SEQ. ID. No. 12) as follows:
VNPIHARFSSVEALRHSNVDIQAIKSEGQLEV-
NGKRYEIRAAADGSIAVLRPDQQSKADKFFKGAA-
HLIGGQSQRAQIAQVLNEKAAAVPRLDRMLGR-
RFDLEKGGSSAVGAAIKAADSRLTSKQTFASFQQ-
WAEKAEALGRYRNRYLHDLQEGHARHNA-
YECGRVKNITWKRYRLSITRKTLSYAPQIHDD-
REEEELDLGRYIAEDRNARTGFFRMVPKDQRA-
PETNSGRLTIGVEPKYGAQLALAMATLMDKHKS-
VTQGKVVGPAKYGQQTDSAILYINGDLAKAVKL-
GEKLKKLSGIPPEGFVEHTPLSMQSTGLGLSYAES-
VEGQPSSHGQARTHVIMDALKGQGPMEN-
RLKMALAERGYDPENPALRARN (375)

Figure 3:
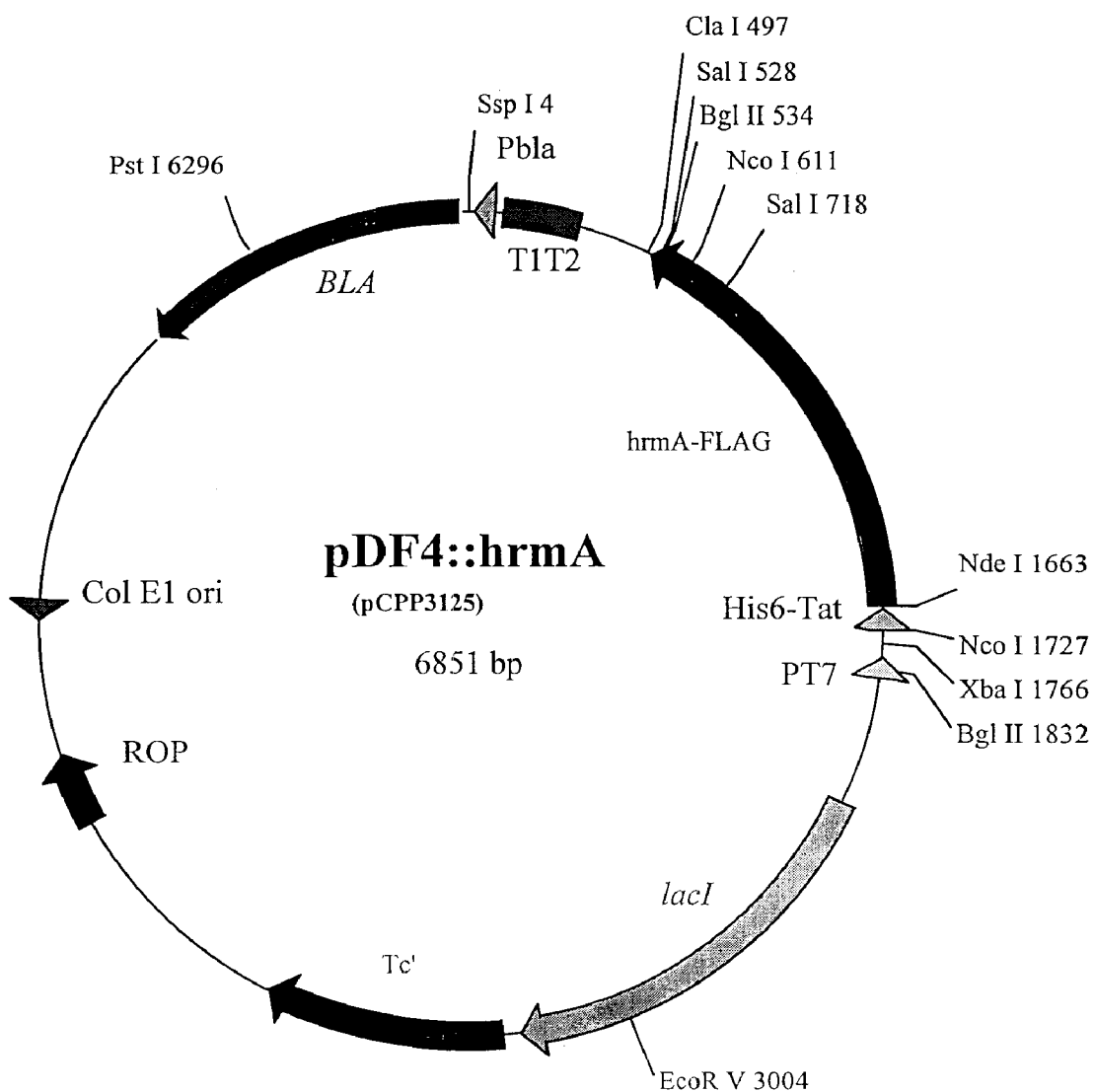
FIG. 3 is a map of plasmid pCPP 3125.

HopPsyA was cloned into pCPP3122 via an NdeI-SSPI fragment from pFLAG-CTC::HopPsyA (pCPP2352) to create pCPP3125 (FIG. 3).

HopPtoA encodes the HopPtoA protein of *Pseudomonas syringae* pv. *tomato* DC300 CEL, and has the following sequence (SEQ. ID. No. 13):
ATGCACATCAACCGACGCGTCCAACAACCGCCTG-
TGACTGCGACGGATAGCTTTCGGACAGCGTCCG-
ACGCGTCTCTTGCCTCCAGCTCTGTGCGATCTGT-
CAGCTCCGATCAGCAACGCGAGATAAATGCG-
ATT GCCGATTACCTGACAGATCATGTGTTCGCTG-
CGCATAAACTGCCGCCGGCCGATTCGGCTGATG-
GCCAAGCTGCAGTTGACGTACACAATGCGC-
AGATCACTGCGCTGATCGAGACGCGCGCCAGCC-
GCCTGCACTTCGAAGGGGAAACCCCGGCAACC-
ATCGCCGACACCTTCGCCAAGGCGGAAAAGCTC-
GACCGATTGGCGACGACTACATCAGGCGCGTT-
GCGGGCGACGCCCTTTGCCATGGCCTCGTTGCT-
TCAGTACATGCAGCCTGCGATCAACAAGGGC-
GATTGGCTGCCGGCTCCGCTCAAACCGCTG-
ACCCCGCTCATTTCCGGAGCGCTGTCGGGCGC-
CATGGACCAGGTGGGCACCAAGATGATGGACC-
GCGCGACGGGTGATCTGCATTACCTGAGCGCCT-
CGCCGGACAGGCTCCACGATGCGATGGCCGCTT-
CGGTGAAGCGCCACTCGCCCAAGCCTTGCTCGA-
CAGGTTCTGGACACGGGGGTTGCGGTTC-
AGACGTACTCGGCGCGCAACGCCGTACGTACCG-
TATTGGCTCCGGCACTGGCGTCCAGACCCGCCG-
TGCAGGGTGCTGTGGACCTTGGTGTATCGATGG-
CGGGTGGTCTGGCTGCCAACGCAGGCTTTG-
GCAACCGCCTGCTCAGTGTGCAGTCGCGTGAT-
CACCAGCGTGGCGGTGCATTAGTGCTCGGTTTG-
AAGGATAAAGAGCCCAAGGCTCAACTGAGC-
GAAGAAAACGACTGGCTCGAGGCTTATAAA-
GCAATCAAATCGGCCAGCTACTCGGGTGCGGCG-
CTCAACGCTGGCAAGCGGATGGCCGGTCTGCC-
ACTGGATATGGCGACCGACGCAATGGGTGCGG-
TAAGAAGCCTGGTGTCAGCGTCCAGCCTGACCC-
AAAACGGTCTGGCCCTGGCGGGTGGCTTT-
GCAGGGGTAGGCAAGTTGCAGGAGATGGCGAC-
GAAAAATATCACCGACCCGGCGACCAAGGCCG-
CGGTCAGTCAGTTGACCAACCTGGCAGGTTCGG-
CAGCCGTTTTCGCAGGCTGGACCACGGCCGCG-
CTGACAACCGATCCCGCGGTGAAAAAAGCCGA-
GTCGTTCATACAGGACACGGTGAAATCG-
ACTGCATCCAGTACCACAGGCTACGTAGCCGACC-
AGACCGTCAAACTGGCGAAGACCGTCAAA-
GACATGGGCGGGGAGGCGATCACCCATACCGGC-
GCCAGCTTGCGCAATACGGTCAATAACCTG-
CGTCAACGCCCGGCTCGTGAAGCTGATATAGAA-
GAGGGGGGCACGGCGGCTTCTCCAAG-
TGAAATACCGTTTCGGCCTATGCGGTCGTAA (1461)

HopPtoA has an amino acid sequence (SEQ. ID. No. 14) as follows:
MHINRRVQQPPVTATDSFRTASDASLASSSVRSVSS-
DQQREINAIADYLTDHVFAAHKLPPADSADG-
QAAVDVHNAQITALIETRASRLHFEGETPATIADTF-
AKAEKLDRLATTTSGALRATPFAMASLLQYMQ-
PAINKGDWLPAPLKPLTPLISGALSGAMDQVGTK-
MMDRATGDLHYLSASPDRLHDAMAASVK-
RHSPSLARQVLDTGVAVQTYSARNAVRTVLAPA-
LASRPAVQGAVDLGVSMAGGLAANAGFGNRLLS-
VQSRDHQRGGALVLGLKDKEPKAQLSEENDWLE-
AYKAIKSASYSGAALNAGKRMAGLPLDMATDA-
MGAVRSLVSASSLTQNGLALAGGFAGVGKLQE-
MATKNITDPATKAAVSQLTNLAGSAAVFAGWTTA-
ALTTDPAVKKAESFIQDTVKSTASSTTGY-
VADQTVKLAKTVKDMGGEAITHTGASL-
RNTVNNLRQRPAREADIEEGGTAASPSEIPFRPMRS (486)

Figure 4:
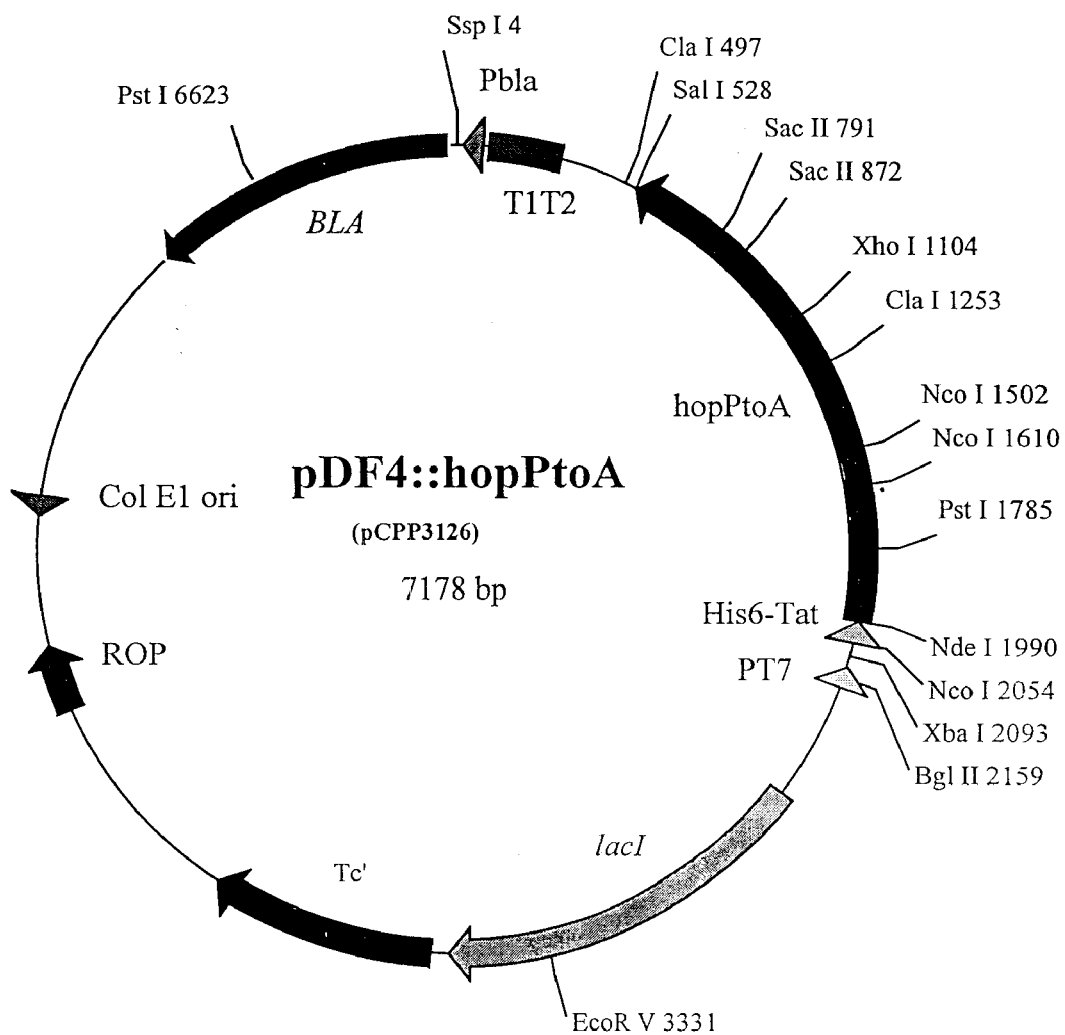
FIG. 4 is a map of plasmid pCPP 3126.

HopPtoA was cloned into pCPP3122 via an NdeI-SalI fragment from pFLAG-CTC::HopPtoA to create pCPP3126 (FIG. 4).

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for delivering effector proteins into a target cell comprising:

introducing into the target cell an effector protein fused to a protein transduction domain of a human immunodeficiency virus TAT protein or derivatives or functional analogs thereof, wherein the effector protein is a protein secreted and/or delivered into eucaryotic cells by a type III secretion system.

2. A method according to claim 1, wherein the target cell is a eucaryotic cell.

3. A method according to claim 1, wherein the effector protein is produced by a bacterial plant pathogen, animal pathogen, or a rhizosphere bacteria.

4. A method according to claim 1, wherein the effector protein is selected from the group consisting of a hypersensitive response elicitor, an avirulence protein, a hypersensitive response and pathogenicity-dependent outer protein, a virulence protein, and a pathogenicity protein.

5. A method according to claim 1, wherein the effector protein is heterologous to the target cell.

6. A method according to claim 1, wherein said introducing comprises:

introducing into the target cell a DNA construct comprising a DNA molecule encoding an effector protein operatively associated with a DNA molecule encoding a protein transduction domain of a human immunodeficiency virus TAT protein or derivatives or functional analogs thereof under conditions effective to express the DNA molecule encoding an effector protein in the target cell.

7. A DNA construct comprising:

a first DNA molecule encoding an effector protein, wherein the effector protein is a protein secreted and/or delivered into eucaryotic cells by a type III secretion system and a second DNA molecule operatively associated with the first DNA molecule and encoding a protein transduction domain of a human immunodeficiency virus TAT protein or derivatives or functional analogs thereof.

8. A DNA construct according to claim 7, wherein the effector protein is produced by a bacterial plant pathogen, animal pathogen, or a rhizosphere bacteria.

9. A DNA construct according to claim 7, wherein the effector protein is selected from the group consisting of a hypersensitive response elicitor, an avirulence protein, a hypersensitive response and pathogenicity-dependent outer protein, a virulence protein, and a pathogenicity protein.

10. A DNA construct according to claim 7, wherein the gene encoding an effector protein is heterologous to the target cell.

11. An isolated target cell transformed with the DNA construct according to claim 7.

* * * * *